United States Patent [19]

Anderson

[11] Patent Number: 4,666,934

[45] Date of Patent: May 19, 1987

[54] PROSTAGLANDIN ANALOGS

[75] Inventor: Bradley D. Anderson, Salt Lake City, Utah

[73] Assignee: The Upjohn Company, Kalamazoo, Mich.

[21] Appl. No.: 747,676

[22] Filed: Jun. 24, 1985

Related U.S. Application Data

[63] Continuation of Ser. No. 571,238, Jan. 16, 1984, abandoned.

[51] Int. Cl.$^4$ .................... C07D 209/42; A61K 31/40
[52] U.S. Cl. ..................................... 514/412; 548/516
[58] Field of Search ......................... 548/516; 514/412

[56] References Cited

U.S. PATENT DOCUMENTS 4,294,759  10/1981  Smith ............................... 260/326.7

OTHER PUBLICATIONS

Berge, S. M., et al., "Pharmaceutical Salts", J. Pharm. Sci. 66, pp. 1-19, 1977.

Primary Examiner—Nicholas S. Rizzo
Attorney, Agent, or Firm—L. Ruth Hattan

[57] ABSTRACT

The compound 6,9-deepoxy-6,9-(phenylimino)-$\Delta^{6,8}$-prostaglandin $I_1$, potassium salt and compositions thereof.

4 Claims, No Drawings

PROSTAGLANDIN ANALOGS

This application is a continuation of application 571,238 filed Jan. 16, 1984, now abandoned.

FIELD OF INVENTION

This invention is the novel compound 6,9-deepoxy-6,9-(phenylimino)-Δ6,8-prostaglandin $I_1$ potassium salt and compositions thereof.

BACKGROUND OF INVENTION

The solid-state chemical stability of a compound sometimes can be influenced by the selection of an appropriate salt form. However, there are no established general principles one can follow in improving solid-state stability through salt modification. For a review of information relating to the selection of "Pharmaceutical Salts" see S. M. Berge, et al., J. Pharm. Sci. 66, pp. 1–19 (1977).

The free acid of 6,9-deepoxy-6,9-(phenylimino)-Δ6,8-prostaglandin $I_1$ and related analogs are known compounds having utility as antiasthmatic agents. See, e.g., U.S. Pat. No. 4,294,759 issued Oct. 13, 1981. The compound of the present invention, i.e., the potassium salt of 6,9-deepoxy-6,9-(phenylimino)-Δ6,8-prostaglandin $I_1$, possesses a number of advantageous physical properties over the free acid rendering said potassium salt a markedly superior product candidate.

SUMMARY OF INVENTION

This invention is the potassium salt of the compound 6,9-deepoxy-6,9-(phenylimino)-Δ6,8-prostaglandin $I_1$, having the structure set forth on the formula sheet as Formula I. The compound and compositions of this invention are useful in the prophylactic or therapeutic treatment of allergy of a reagin or non-reagin mediated nature. Thus the compound and compositions of the present invention are useful in treating asthma, as well as allergic rhinitis, food allergy and urticaria.

DETAILED DESCRIPTION OF INVENTION

The potassium salt of 6,9-deepoxy-6,9-(phenylimino)-Δ6,8-prostaglandin $I_1$ is useful in the same manner and is administered in the same manner and at the same dosage as is described for the pharmaceutically useful compounds described and claimed in U.S. Pat. No. 4,294,759. Also, pharmaceutical compositions of the potassium salt of 6,9-deepoxy-6,9-(phenylimino)-Δ6,8-prostaglandin $I_1$ are useful in the same manner, and are of the same type and are prepared in the same manner as the compositions described in U.S. Pat. No. 4,294,759. The disclosure of U.S. Pat. No. 4,294,759 and in particular the portion appearing on from column 12, line 14 through column 14, line 53 is incorporated herein by reference.

The compound of this invention is also useful in preventing or inhibiting the hypersecretion of mucus in the respiratory tract of warm blooded animals as generally described in U.S. application Ser. No. 529,798, filed Sept. 6, 1983, now abandoned.

The potassium salt of the compound 6,9-deepoxy-6,9-(phenylimino)-Δ6,8-prostaglandin $I_1$ possesses advantageous physical properties including ease of crystallization, high melting point, high water solubility, and low solubility in fluorinated and fluorochlorinated liquified propellants as compared to the free acid of said compound. More significantly the potassium salt of 6,9-deepoxy-6,9-(phenylimino)-Δ6,8-prostaglandin $I_1$ unexpectedly exhibits an improved solid-state stability over the free acid or the sodium salt. The following tabulations of data demonstrate the differences in the physicochemical characteristics of the free acid, the sodium salt and the potassium salt of 6,9-deepoxy-6,9-(phenylimino)-Δ6,8-prostaglandin $I_1$. As a result of the physical properties of the potassium salt it offers significant advantages over the corresponding free acid or sodium salt, for example, in the long term storage of bulk drug and in prolonging the shelf-life of pharmaceutically useful formulations of said salt form, such as, suspension formulations for aerosol administration.

TABLE I

Physico-Chemical Data

| | Property | Value Desired | Free Acid | Sodium Salt | Potassium Salt |
|---|---|---|---|---|---|
| 1 | Ease of synthesis | Easily crystallized | — | Acceptable | Acceptable |
| 2 | Characterizability | Passes profile (+ low moisture content after air equilibration) | Pass | (.82% $H_2O$)[a] | Pass (.42% $H_2O$) |
| 3 | Water solubility | Dissolves readily in water | 1 μg/ml | Soluble | Soluble |
| 4 | Trichlorotrifluoroethane solubility | Low | .38 μg/ml | — | 0.43 μg/ml |
| 5 | Melting point (micronizability) | High (>100° C.) | 135–140 | >175 | >175 |
| 6 | Solild state stability (see Table II) | <2% degradation (2 months at 33° C.) | >10% | >>50% | <2% |
| 7 | Specific | 1.3–1.6[b] | — | 1.18 | 1.20 |

TABLE I-continued

| | Physico-Chemical Data | | | |
|---|---|---|---|---|
| Property | Value Desired | Free Acid | Sodium Salt | Potassium Salt |
| gravity | | | | |

[a]Initial analysis acceptable but later assays (HPLC) unacceptable due to solid-state decomposition.
[b]Specific gravities below this range may require incorporation of other high density solids into an aersol suspension.

TABLE II

Solid-State Stability

| | | Percent of Theory | | |

Materials (a) to (c) are packaged in suitable (aluminum) containers equipped with a metering valve designed to meter 50 mcl per dose, an equivalent of 0.5 mg of compound (a).

EXAMPLE 4

To prepare a typical powder for inhalation, 2 g of 6,9-deepoxy-6,9-(phenylimino)-Δ6